US012691059B2

(12) United States Patent
Gerardi et al.

(10) Patent No.: US 12,691,059 B2
(45) **Date of Patent: *Jul. 28, 2026**

(54) ORAL COMPOSITION WITH POLYMERIC COMPONENT

(71) Applicant: NICOVENTURES TRADING LIMITED, London (GB)

(72) Inventors: Anthony Richard Gerardi, Winston-Salem, NC (US); Andries Don Sebastian, Winston-Salem, NC (US); Ronald K. Hutchens, East Bend, NC (US); John Paul Mua, Advance, NC (US); Darrell Eugene Holton, Jr., Clemmons, NC (US); Christopher Keller, Advance, NC (US); Thomas H. Poole, Winston-Salem, NC (US); Dwayne William Beeson, Kernersville, NC (US); Frank Kelley St. Charles, Bowling Green, KY (US); John E. Bunch, Cary, NC (US); Luis Monsalud, Kernersville, NC (US)

(73) Assignee: NICOVENTURES TRADING LIMITED, London (GB)

( * ) Notice: Subject to any disclaimer, the term of this patent is extended or adjusted under 35 U.S.C. 154(b) by 199 days.

This patent is subject to a terminal disclaimer.

(21) Appl. No.: 17/834,989

(22) Filed: Jun. 8, 2022

(65) Prior Publication Data

US 2022/0296501 A1     Sep. 22, 2022

Related U.S. Application Data

(63) Continuation of application No. PCT/IB2020/061655, filed on Dec. 8, 2020, which is a continuation-in-part of application No. 16/707,154, filed on Dec. 9, 2019, now abandoned.

(51) Int. Cl.
| | |
|---|---|
| *A61K 9/00* | (2006.01) |
| *A61K 31/197* | (2006.01) |
| *A61K 31/198* | (2006.01) |
| *A61K 31/522* | (2006.01) |
| *A61K 36/185* | (2006.01) |
| *A61K 36/53* | (2006.01) |
| *A61K 36/605* | (2006.01) |
| *A61K 36/82* | (2006.01) |
| *A61K 36/9066* | (2006.01) |
| *A61K 47/36* | (2006.01) |
| *A61K 47/38* | (2006.01) |

(52) U.S. Cl.
CPC ............ *A61K 9/009* (2013.01); *A61K 9/0056* (2013.01); *A61K 31/197* (2013.01); *A61K 31/198* (2013.01); *A61K 31/522* (2013.01); *A61K 36/3482* (2024.05); *A61K 36/53* (2013.01); *A61K 36/605* (2013.01); *A61K 36/82* (2013.01); *A61K 36/9066* (2013.01); *A61K 47/36* (2013.01); *A61K 47/38* (2013.01)

(58) Field of Classification Search
CPC .... A61K 9/009; A61K 9/0056; A61K 31/197; A61K 31/198; A61K 31/522; A61K 36/53; A61K 36/605; A61K 36/82; A61K 36/9066; A61K 47/36; A61K 47/38
See application file for complete search history.

(56) References Cited

U.S. PATENT DOCUMENTS

| | | | |
|---|---|---|---|
| 5,417,229 A | 5/1995 | Summers et al. |
| 6,138,683 A | 10/2000 | Hersh et al. |
| 6,845,777 B2 | 1/2005 | Pera |
| 6,958,143 B2 | 10/2005 | Choi et al. |
| 7,032,601 B2 | 4/2006 | Atchley et al. |
| 7,056,541 B1 | 6/2006 | Stahl et al. |
| 7,507,427 B2 | 3/2009 | Andersen et al. |
| 7,810,507 B2 | 10/2010 | Dube et al. |
| 7,833,555 B2 | 11/2010 | Andersen et al. |

(Continued)

FOREIGN PATENT DOCUMENTS

| | | |
|---|---|---|
| CN | 103005680 | 4/2013 |
| CN | 103263507 | 8/2013 |

(Continued)

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.
Shit, Subhas et al., "Edible Polymers: Challenges and Opportunities", Journal of Polymers vol. 2014, Article ID 427259, 13 pages; http://dx.doi.org/10.1155/2014/427259.
Vieira, Melissa et al., "Natural-based plasticizers and biopolymer films: A review", European Polymer Journal 47, (2011), 254-263.

*Primary Examiner* — Robert A Wax
*Assistant Examiner* — Olga V. Tcherkasskaya
(74) *Attorney, Agent, or Firm* — WOMBLE BOND DICKINSON (US) LLP; Scott R. Breining

(57) ABSTRACT

The disclosure provides oral compositions including at least one active ingredient and a polymeric component, the oral compositions having a moisture content of at least about 10% by weight, based on total weight of the oral composition. The polymeric component includes a natural gum, a food grade polymer, or a combination thereof. The natural gum may be a non-galactomannan polysaccharide; a galactomannan polysaccharide selected from fenugreek gum, tara gum, locust bean gum, cassia gum, and combinations thereof, or a combination of guar gum and a second natural gum. The food grade polymer may be selected from proteins, synthetic polymers, non-cellulosic polysaccharides which are not natural gums, and combinations thereof.

12 Claims, 1 Drawing Sheet

(56)                    References Cited

U.S. PATENT DOCUMENTS

| | | |
|---|---|---|
| 7,861,728 B2 | 1/2011 | Holton, Jr. et al. |
| 7,900,637 B2 | 3/2011 | Fagerstrom et al. |
| 7,950,399 B2 | 5/2011 | Winterson et al. |
| 8,069,861 B2 | 12/2011 | Sinclair |
| 8,124,147 B2 | 2/2012 | Cheng et al. |
| 8,293,295 B2 | 10/2012 | Andersen et al. |
| 8,336,557 B2 | 12/2012 | Kumar et al. |
| 8,343,532 B2 | 1/2013 | Dam et al. |
| 8,424,541 B2 | 4/2013 | Crawford et al. |
| 8,469,036 B2 | 6/2013 | Williams et al. |
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hansson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,334,873 B2 | 7/2019 | Mishra et al. |
| 10,357,054 B2 | 7/2019 | Marshall et al. |
| 10,375,984 B2 | 8/2019 | Hernandez Garcia et al. |
| 10,426,726 B2 | 10/2019 | Neergaard |
| 10,463,070 B2 | 11/2019 | Carroll et al. |
| 10,532,046 B2 | 1/2020 | Rogers et al. |
| 10,543,205 B2 | 1/2020 | Wittorff et al. |
| 10,959,456 B2 | 3/2021 | Sebastian et al. |
| 2003/0224090 A1 | 12/2003 | Pearce et al. |
| 2004/0118422 A1 | 6/2004 | Lundin et al. |
| 2006/0147498 A1 | 7/2006 | Jonsson et al. |
| 2007/0031539 A1 | 2/2007 | Calton |
| 2008/0081071 A1 | 4/2008 | Sanghvi et al. |
| 2008/0166395 A1 | 7/2008 | Roush |
| 2009/0022917 A1 | 1/2009 | Gedevanishvili et al. |
| 2009/0023819 A1 | 1/2009 | Axelsson |
| 2009/0065013 A1 | 3/2009 | Essen et al. |
| 2009/0253754 A1 | 10/2009 | Selmin et al. |
| 2009/0301504 A1 | 12/2009 | Worthen et al. |
| 2010/0004294 A1 | 1/2010 | Axelsson et al. |
| 2010/0061940 A1 | 3/2010 | Axelsson et al. |
| 2010/0187143 A1 | 7/2010 | Essen et al. |
| 2010/0218779 A1 | 9/2010 | Zhuang et al. |
| 2010/0260690 A1 | 10/2010 | Kristensen et al. |
| 2010/0291245 A1 | 11/2010 | Gao et al. |
| 2010/0294292 A1 | 11/2010 | Hodin et al. |
| 2011/0139164 A1 | 6/2011 | Mua et al. |
| 2011/0220130 A1 | 9/2011 | Mua et al. |
| 2011/0232662 A1 | 9/2011 | Liu et al. |
| 2011/0268809 A1 | 11/2011 | Brinkley et al. |
| 2012/0031415 A1 | 2/2012 | Essen et al. |
| 2012/0037175 A1 | 2/2012 | Cantrell et al. |
| 2013/0078307 A1 | 3/2013 | Holton, Jr. et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206150 A1 | 8/2013 | Duggins et al. |
| 2013/0251779 A1 | 9/2013 | Svandal et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0255452 A1 | 9/2014 | Reddick et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0101627 A1 | 4/2015 | Marshall et al. |
| 2015/0296868 A1 | 10/2015 | Sutton |
| 2016/0000140 A1 | 1/2016 | Sebastian et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0192703 A1 | 7/2016 | Sebastian et al. |
| 2017/0007594 A1 | 1/2017 | Borschke |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0280764 A1 | 10/2017 | Sahlen et al. |
| 2017/0312261 A1 | 11/2017 | Changoer et al. |
| 2017/0318858 A1 | 11/2017 | Hodin et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2019/0037909 A1 | 2/2019 | Greenbaum et al. |
| 2019/0255035 A1 | 8/2019 | Bruun |
| 2020/0037638 A1 | 2/2020 | Faraci et al. |
| 2020/0128870 A1 | 4/2020 | Hassler et al. |
| 2020/0138706 A1 | 5/2020 | Rudraraju et al. |
| 2020/0275689 A1 | 9/2020 | Lewerenz |
| 2020/0297026 A1 | 9/2020 | Kannisto et al. |

(56)  References Cited

U.S. PATENT DOCUMENTS

| 2020/0305496 | A1  |     | 10/2020 | Gessesse |          |
|---|---|---|---|---|---|
| 2021/0068446 | A1 | * | 3/2021 | Keller | .................... A24B 15/30 |

FOREIGN PATENT DOCUMENTS

| CN | 103494324 |     | 1/2014 |
|---|---|---|---|
| CN | 105192876 |     | 12/2015 |
| CN | 105595404 |     | 5/2016 |
| RU | 2415599 | C1 | 10/2011 |
| WO | WO2009/108769 |     | 9/2009 |
| WO | WO2019/036243 |     | 2/2019 |

* cited by examiner

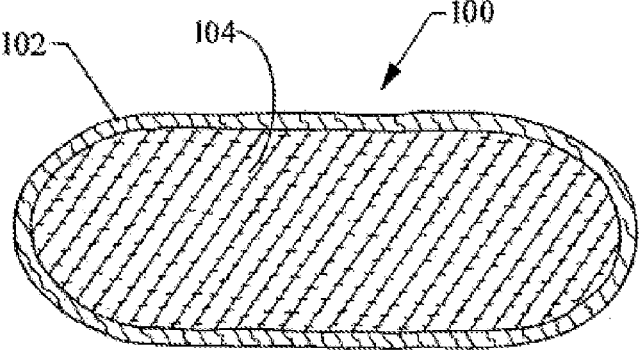

ORAL COMPOSITION WITH POLYMERIC COMPONENT

CROSS-REFERENCE TO RELATED APPLICATIONS

This application is a continuation of International Application No. PCT/IB2020/061655, filed Dec. 8, 2020, and is a continuation in part of U.S. patent application Ser. No. 16/707,154, filed Dec. 9, 2019, each of which are herein incorporated by reference in their entirety.

FIELD OF THE DISCLOSURE

The present disclosure relates to flavored products intended for human use. The products are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known.

See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free.

BRIEF SUMMARY

The present disclosure generally provides products configured for oral use which comprise at least one active ingredient, a flavorant, or a combination thereof, and a polymeric component. The products are intended to impart a taste when used orally and to deliver substances to the consumer, for example, nicotine or other active ingredients. Accordingly, in one aspect, the disclosure provides an oral composition comprising at least one active ingredient, a flavorant, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof, and wherein the composition has a moisture content of at least about 10% by weight, based on total weight of the oral composition.

In some embodiments, the natural gum is a non-galactomannan polysaccharide selected from the group consisting of acacia gum, xanthan gum, pullulan, gellan gum, tragacanth gum, gum karaya, and combinations thereof. In some embodiments, the natural gum is a galactomannan polysaccharide selected from the group consisting of fenugreek gum, tara gum, locust bean gum, cassia gum, and combinations thereof. In some embodiments, the natural gum is a combination of guar gum and a second natural gum, wherein the second natural gum is a galactomannan or non-galactomannan polysaccharide. In some embodiments, the natural gum is present in a range of from about 0.1% to about 80% by weight, based on total weight of the oral composition.

In some embodiments, the oral composition comprises at least one active ingredient, and the polymeric component is a food grade polymer. In some embodiments, the food grade polymer is a synthetic polymer, chitin, chitosan, carrageenan, alginate, pectin, casein, whey protein, soy protein isolate, collagen, rubisco, gelatin, lentil protein, peanut protein, mung bean protein, or a combination thereof. In some embodiments, the food grade polymer is pectin. In some embodiments, the synthetic polymer is polyvinyl alcohol, low density polyethylene, oriented polypropylene, polyethylene terephthalate, polyvinylidene chloride, or a combination thereof.

In some embodiments, the oral composition comprises at least one active ingredient, wherein the polymeric component is a combination of guar gum and a second natural gum, and wherein the second natural gum is selected from the group consisting of xanthan gum, pullulan, gellan gum, and combinations thereof. In some embodiments, the ratio by weight of guar gum to the second natural gum is from about 0.1 to about 1.0.

In some embodiments, the oral composition further comprises a filler. In some embodiments, the filler comprises cellulose, a cellulose derivative, a starch, or a combination thereof. In some embodiments, the filler is microcrystalline cellulose (MCC). In some embodiments, the MCC is present in an amount of from about 1% to about 60% by weight, based on the total weight of the composition.

In some embodiments, the active ingredient comprises one or more botanical materials, stimulants, nicotine components, amino acids, vitamins, antioxidants, cannabinoids, cannabimimetics, terpenes, pharmaceutical agents, nutraceuticals, or a combination thereof. In some embodiments, the active ingredient is selected from the group consisting of caffeine, taurine, theanine, and combinations thereof.

In some embodiments, the oral composition is substantially free of one or more of xanthan gum, tobacco materials, and nicotine components.

In some embodiments, the oral composition is in the form of a chewable oral product, the chewable oral product having a moisture content of from about 10% to about 60% by weight, based on total weight of the chewable oral product, wherein a water activity of the chewable oral product is less than about 0.85.

In some embodiments, the oral composition is enclosed in a pouch to form a pouched product.

In another aspect is provided an oral composition enclosed in a pouch to form a pouched product, the oral composition comprising: at least one active ingredient comprising one or more botanical materials, caffeine, amino acids, vitamins, amino acids, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof; and wherein the composition has a moisture content of at least about 10% by weight, based on total weight of the oral composition.

In some embodiments, the natural gum is a non-galactomannan polysaccharide selected from the group consisting of acacia gum, xanthan gum, pullulan, gellan gum, tragacanth gum, gum karaya, and combinations thereof.

In some embodiments, wherein the natural gum is a galactomannan polysaccharide selected from the group consisting of fenugreek gum, tara gum, locust bean gum, cassia gum, and combinations thereof.

In some embodiments, the natural gum is a combination of guar gum and a second natural gum, wherein the second natural gum is a galactomannan or non-galactomannan polysaccharide.

In some embodiments, the natural gum is present in a range of from about 0.1% to about 80% by weight, based on total weight of the oral composition.

In some embodiments, the polymeric component is a food grade polymer.

In some embodiments, the food grade polymer is a synthetic polymer, chitin, chitosan, carrageenan, alginate, pectin, casein, whey protein, soy protein isolate, collagen, rubisco, gelatin, lentil protein, peanut protein, mung bean protein, or a combination thereof. In some embodiments, the food grade polymer is pectin. In some embodiments, the synthetic polymer is polyvinyl alcohol, low density polyethylene, oriented polypropylene, polyethylene terephthalate, polyvinylidene chloride, or a combination thereof.

In some embodiments, the polymeric component is a combination of guar gum and a second natural gum, wherein the second natural gum is selected from the group consisting of xanthan gum, pullulan, gellan gum, and combinations thereof. In some embodiments, the ratio by weight of guar gum to the second natural gum is from about 0.01 to about 10.

In some embodiments, the oral composition further comprises a filler. In some embodiments, the filler comprises cellulose, a cellulose derivative, a starch, or a combination thereof. In some embodiments, the filler is microcrystalline cellulose (MCC). In some embodiments, the MCC is present in an amount of from about 1% to about 60% by weight, based on the total weight of the composition.

In some embodiments, the oral composition is substantially free of one or more of xanthan gum, tobacco materials, and nicotine components.

In some embodiments, the at least one active ingredient is a combination of green tea, turmeric, and white mulberry.

In some embodiments, the at least one active ingredient is a combination of theanine, gamma-amino butyric acid (GABA), and lemon balm extract.

In another aspect is provided an oral composition in the form of a chewable oral product, the chewable oral product having a moisture content of from about 15% to about 60% by weight, based on total weight of the chewable oral product; and wherein a water activity of the chewable oral product is less than about 0.85, the oral composition comprising: at least one active ingredient comprising one or more botanical materials, caffeine, amino acids, vitamins, amino acids, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; and wherein the food grade polymer is selected from the group consisting of proteins, synthetic polymers, non-cellulosic polysaccharides which are not natural gums, and combinations thereof.

In some embodiments, the chewable oral product comprises a polymeric component comprising a natural gum, wherein: the natural gum is a galactomannan polysaccharide selected from the group consisting of fenugreek gum, tara gum, locust bean gum, cassia gum, and combinations thereof, or the natural gum is a combination of guar gum and a second natural gum selected from the group consisting of xanthan gum, pullulan, gellan gum, and combinations thereof.

The disclosure includes, without limitations, the following embodiments.

Embodiment 1: An oral composition comprising: at least one active ingredient, a flavorant, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof, and wherein the composition has a moisture content of at least about 10% by weight, based on total weight of the oral composition.

Embodiment 2: The oral composition of embodiment 1, wherein the natural gum is a non-galactomannan polysaccharide selected from the group consisting of acacia gum, xanthan gum, pullulan, gellan gum, tragacanth gum, gum karaya, and combinations thereof.

Embodiment 3: The oral composition of embodiment 1 or 2, wherein the natural gum is a galactomannan polysaccharide selected from the group consisting of fenugreek gum, tara gum, locust bean gum, cassia gum, and combinations thereof.

Embodiment 4: The oral composition of any one of embodiments 1 to 3, wherein the natural gum is a combination of guar gum and a second natural gum, wherein the second natural gum is a galactomannan or non-galactomannan polysaccharide.

Embodiment 5: The oral composition of any one of embodiments 1 to 4, wherein the natural gum is present in a range of from about 0.1% to about 80% by weight, based on total weight of the oral composition.

Embodiment 6: The oral composition of any one of embodiments 1 to 5, comprising at least one active ingredient, wherein the polymeric component is a food grade polymer.

Embodiment 7: The oral composition of any one of embodiments 1 to 6, wherein the food grade polymer is a synthetic polymer, chitin, chitosan, carrageenan, alginate, pectin, casein, whey protein, soy protein isolate, collagen, rubisco, gelatin, lentil protein, peanut protein, mung bean protein, or a combination thereof.

Embodiment 8: The oral composition of any one of embodiments 1 to 7, wherein the food grade polymer is pectin.

Embodiment 9: The oral composition of any one of embodiments 1 to 8, wherein the synthetic polymer is polyvinyl alcohol, low density polyethylene, oriented polypropylene, polyethylene terephthalate, polyvinylidene chloride, or a combination thereof.

Embodiment 10: The oral composition of any one of embodiments 1 to 9, comprising at least one active ingredient, wherein the polymeric component is a combination of guar gum and a second natural gum, wherein the second natural gum is selected from the group consisting of xanthan gum, pullulan, gellan gum, and combinations thereof.

Embodiment 11: The oral composition of any one of embodiments 1 to 10, wherein the ratio by weight of guar gum to the second natural gum is from about 0.01 to about 10.

Embodiment 12: The oral composition of any one of embodiments 1 to 11, wherein the natural gum is a combination of guar gum and a second natural gum selected from the group consisting of xanthan gum, pullulan, and gellan gum, wherein the ratio of guar gum to the second natural gum is from about 0.01 to about 10.

Embodiment 13: The oral composition of any one of embodiments 1 to 12, wherein the natural gum is a combination of guar or locust bean gum with xanthan, wherein the ratio by weight of guar gum or locust bean gum to xanthan gum is from about 1 to about 10.

Embodiment 14: The oral composition of any one of embodiments 1 to 13, wherein the natural gum is a combination of guar or locust bean gum with pullulan, wherein the ratio of guar or locust bean gum to pullulan is from about 1 to about 10.

Embodiment 15: The oral composition of any one of embodiments 1 to 14, wherein the natural gum is a combination of guar, xanthan and pullulan wherein the ratio by weight of guar gum to xanthan gum to pullulan is from about 1:1:1 to about 10:1:1.

Embodiment 16: The oral composition of any one of embodiments 1 to 15, further comprising a filler.

Embodiment 17: The oral composition of any one of embodiments 1 to 16, wherein the filler comprises cellulose, a cellulose derivative, a starch, or a combination thereof.

Embodiment 18: The oral composition of any one of embodiments 1 to 17, wherein the filler is microcrystalline cellulose (MCC).

Embodiment 19: The oral composition of any one of embodiments 1 to 18, wherein the MCC is present in an amount of from about 1% to about 60% by weight, based on the total weight of the composition.

Embodiment 20: The oral composition of any one of embodiments 1 to 19, wherein the active ingredient comprises one or more botanical materials, stimulants, nicotine components, amino acids, vitamins, antioxidants, cannabinoids, cannabimimetics, terpenes, pharmaceutical agents, nutraceuticals, or a combination thereof.

Embodiment 21: The oral composition of any one of embodiments 1 to 20, wherein the active ingredient is selected from the group consisting of caffeine, taurine, theanine, theobromine, and combinations thereof.

Embodiment 22: The oral composition of any one of embodiments 1 to 21, wherein the flavorant is selected from the group consisting of mint, fruit flavors, limonene, star anise, eucalyptus, menthol, and combinations thereof.

Embodiment 23: The oral composition of any one of embodiments 1 to 22, wherein the oral composition is substantially free of one or more of xanthan gum, tobacco materials, and nicotine components.

Embodiment 24: The oral composition of any one of embodiments 1 to 23, in the form of a chewable oral product, the chewable oral product having a moisture content of from about 10% to about 60% by weight, based on total weight of the chewable oral product; and wherein a water activity of the chewable oral product is less than about 0.85.

Embodiment 25: The oral composition of any one of embodiments 1 to 24, wherein the composition is enclosed in a pouch to form a pouched product.

Embodiment 26: An oral composition configured to deliver an active ingredient to a user through contact with moisture in the mouth of the user, the composition comprising at least one active ingredient, a flavorant, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof; or a combination of guar gum and a second natural gum; wherein the food grade polymer is selected from the group consisting of proteins, synthetic polymers, non-cellulosic polysaccharides which are not natural gums, and combinations thereof, and wherein the composition has a moisture content of at least about 10% by weight, based on total weight of the oral composition.

Embodiment 27: A method of preparing an oral composition comprising at least one active ingredient, a flavorant, or a combination thereof, a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof; or a combination of guar gum and a second natural gum; wherein the food grade polymer is selected from the group consisting of proteins, synthetic polymers, non-cellulosic polysaccharides which are not natural gums, and combinations thereof, and wherein the composition has a moisture content of at least about 10% by weight, based on total weight of the oral composition; the method comprising combining the at least one active ingredient, flavorant, or combination thereof with the polymeric component and sufficient water to provide a moisture content of the oral composition of at least about 10% by weight, based on total weight of the oral composition.

Embodiment 28: A method of modifying a property of an oral composition comprising at least one active ingredient, a flavorant, or a combination thereof, and a polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof; and wherein the composition has a moisture content of at least about 10% by weight, based on total weight of the oral composition; the method comprising selecting the polymeric component wherein the property is one or more of texture, mouthfeel, cohesiveness, compressibility, and the length of time over which the active ingredient, the flavorant, or both, are released from the composition.

Embodiment 29: A polymeric component for use in an oral composition comprising at least one active ingredient, a flavorant, or a combination thereof, the polymeric component comprising a natural gum, a food grade polymer, or a combination thereof, wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof.

Embodiment 30: An oral composition enclosed in a pouch to form a pouched product, the oral composition comprising: at least one active ingredient comprising one or more botanical materials, caffeine, amino acids, vitamins, amino acids, or a combination thereof, a polymeric component comprising a natural gum, a food grade polymer, or a combination thereof, wherein the natural gum is a non-galactomannan polysaccharide;—a galactomannan polysaccharide selected from the group consisting of fenugreek gum, tara gum, locust bean gum, cassia gum, and combinations thereof, or a combination of guar gum and a second natural gum; wherein the food grade polymer is selected from the group consisting of proteins, synthetic polymers, non-cellulosic polysaccharides which are not natural gums, and combinations thereof; and wherein the composition has a moisture content of at least about 10% by weight, based on total weight of the oral composition.

Embodiment 31: The oral composition of embodiment 30, wherein the natural gum is a non-galactomannan polysaccharide selected from the group consisting of acacia gum, xanthan gum, pullulan, gellan gum, tragacanth gum, gum karaya, and combinations thereof.

Embodiment 32: The oral composition of embodiment 30, wherein the natural gum is a galactomannan polysaccharide selected from the group consisting of fenugreek gum, tara gum, locust bean gum, cassia gum, and combinations thereof.

Embodiment 33: The oral composition of embodiment 30, wherein the natural gum is a combination of guar gum and a second natural gum, wherein the second natural gum is a galactomannan or non-galactomannan polysaccharide.

Embodiment 34: The oral composition of embodiment 30, wherein the natural gum is present in a range of from about 0.1% to about 80% by weight, based on total weight of the oral composition.

Embodiment 35: The oral composition of embodiment 30, wherein the polymeric component is a food grade polymer.

Embodiment 36: The oral composition of embodiment 35, wherein the food grade polymer is a synthetic polymer, chitin, chitosan, carrageenan, alginate, pectin, casein, whey protein, soy protein isolate, collagen, rubisco, gelatin, lentil protein, peanut protein, mung bean protein, or a combination thereof.

Embodiment 37: The oral composition of embodiment 35, wherein the food grade polymer is pectin.

Embodiment 38: The oral composition of embodiment 36, wherein the synthetic polymer is polyvinyl alcohol, low density polyethylene, oriented polypropylene, polyethylene terephthalate, polyvinylidene chloride, or a combination thereof.

Embodiment 39: The oral composition of embodiment 30, wherein the polymeric component is a combination of guar gum and a second natural gum, wherein the second natural gum is selected from the group consisting of xanthan gum, pullulan, gellan gum, and combinations thereof.

Embodiment 40: The oral composition of embodiment 39, wherein the ratio by weight of guar gum to the second natural gum is from about 0.01 to about 10.

Embodiment 41: The oral composition of any one of embodiments 30-40, further comprising a filler.

Embodiment 42: The oral composition of embodiment 41, wherein the filler comprises cellulose, a cellulose derivative, a starch, or a combination thereof.

Embodiment 43: The oral composition of embodiment 41, wherein the filler is microcrystalline cellulose (MCC).

Embodiment 44: The oral composition of embodiment 43, wherein the MCC is present in an amount of from about 1% to about 60% by weight, based on the total weight of the composition.

Embodiment 45: The oral composition of any one of embodiments 30-44, wherein the oral composition is substantially free of one or more of xanthan gum, tobacco materials, and nicotine components.

Embodiment 46: The oral composition of any one of embodiments 30-45, wherein the at least one active ingredient is a combination of green tea, turmeric, and white mulberry.

Embodiment 47: The oral composition of any one of embodiments 30-45, wherein the at least one active ingredient is a combination of theanine, gamma-amino butyric acid (GABA), and lemon balm extract.

Embodiment 48: An oral composition in the form of a chewable oral product, the chewable oral product having a moisture content of from about 15% to about 60% by weight, based on total weight of the chewable oral product; and wherein a water activity of the chewable oral product is less than about 0.85, the oral composition comprising: at least one active ingredient comprising one or more botanical materials, caffeine, amino acids, vitamins, amino acids, or a combination thereof, a polymeric component comprising a natural gum, a food grade polymer, or a combination thereof; wherein the natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum; and wherein the food grade polymer is selected from the group consisting of proteins, synthetic polymers, non-cellulosic polysaccharides which are not natural gums, and combinations thereof.

Embodiment 49: The oral composition of embodiment 48, the chewable oral product comprising a polymeric component comprising a natural gum, wherein: the natural gum is a galactomannan polysaccharide selected from the group consisting of fenugreek gum, tara gum, locust bean gum, cassia gum, and combinations thereof, or the natural gum is a combination of guar gum and a second natural gum selected from the group consisting of xanthan gum, pullulan, gellan gum, and combinations thereof.

Embodiment 50: The oral composition of embodiment 48 or 49, wherein the at least one active ingredient is a combination of green tea, turmeric, and white mulberry.

These and other features, aspects, and advantages of the disclosure will be apparent from a reading of the following detailed description together with the accompanying drawing, which is briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Having thus described aspects of the disclosure in the foregoing general terms, reference will now be made to the accompanying drawing, which is not necessarily drawn to scale. The drawing is exemplary only, and should not be construed as limiting the disclosure.

FIG. 1 is a perspective view of a pouched product embodiment, taken across the width of the product, showing an outer pouch filled with an oral composition of the present disclosure.

DETAILED DESCRIPTION

The present disclosure provides oral compositions comprising at least one active ingredient, a flavorant, or a combination thereof, a polymeric component comprising a natural gum, a food grade polymer, or a combination thereof, wherein the composition has a moisture content of at least about 10% by weight, based on total weight of the oral composition. The natural gum is a non-galactomannan polysaccharide; a galactomannan polysaccharide selected from the group consisting of fenugreek gum, tara gum, locust bean gum, cassia gum, and combinations thereof, or a combination of guar gum and a second natural gum. The food grade polymer is selected from the group consisting of proteins, synthetic polymers, non-cellulosic polysaccharides which are not natural gums, and combinations thereof.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The products as described herein comprise at least one active ingredient, a flavorant, or a combination thereof and a polymeric component, wherein the composition has a moisture content of at least about 10% by weight, based on total weight of the oral composition. The relative amounts of the various components within the oral composition may vary, and typically are selected so as to provide the desired sensory and performance characteristics to the oral composition. The example individual components of the oral composition are described herein below.

Polymeric Component

Oral compositions as described herein comprise a polymeric component. Such polymeric components may fulfill multiple functions, such as enhancing certain organoleptic properties such as texture and mouthfeel, enhancing cohesiveness or compressibility of the composition, adding bulk to the composition, acting as a carrier for an active ingredient or flavorant, and the like.

The quantity of the polymeric component present in oral compositions as described herein may vary according to the desired properties, but is generally present in an amount sufficient to provide the desired physical attributes and physical integrity to the composition. The amount of polymeric component on a weight basis can vary, but is typically up to about 80% of the total composition by weight. A typical range of polymeric component within the oral composition can be from about 0.1% to about 80% by total weight of the composition, for example, from about 0.1 to about 1, or from about 1 to about 10, or from about 10 to about 80% by weight. In some embodiments, the polymeric component is present in the oral composition in an amount by weight of from about 0.1 to about 1%, for example, about 0.1, about 0.2, about 0.3, about 0.4, about 0.5, about 0.6, about 0.7, about 0.8, about 0.9, or about 1% by weight, based on the total weight of the oral composition. In some embodiments, the polymeric component is present in the oral composition in an amount by weight of from about 1 to about 10%, for example, about 1, about 2, about 3, about 4, about 5, about 6, about 7, about 8, about 9, or about 10% by weight, based on the total weight of the oral composition. In some embodiments, the polymeric component is present in the oral composition in an amount by weight of from about 10 to about 75%, for example, about 10, about 15, about 20, about 25, or about 30, to about 35, about 40, about 45, about 50, about 55, about 60, about 65, about 70, about 75%, or about 80% by weight (e.g., about 15 to about 60% by weight, or about 25 to about 45% by weight) based on the total weight of the composition.

In some embodiments, the polymeric component comprises a natural gum. As used herein, "natural gum" refers to polysaccharide materials of natural origin that are useful as thickening or gelling agents. Representative natural gums derived from plants, which are typically water soluble to some degree, include acacia gum (gum Arabic), xanthan gum, guar gum, ghatti gum, gum tragacanth, karaya gum, locust bean gum, pullulan, and gellan gum. Natural gums may be galactomannan polysaccharides or non-galactomannan polysaccharides. Galactomannan polysaccharides consist of a mannose backbone with galactose side groups. More specifically, galactomannan polysaccharides possess a (1-4)-linked β-D-mannopyranose backbone with branch points at the 6-positions linked to α-D-galactose (i.e. 1-6-linked α-D-galactopyranose).

In some embodiments, the natural gum is a non-galactomannan polysaccharide. Examples of non-galactomannan polysaccharides which are natural gums include acacia gum, xanthan gum, pullulan, ghatti gum, gum tragacanth, karaya gum, and gellan gum. In some embodiments, the natural gum is a non-galactomannan polysaccharide selected from the group consisting of acacia gum, xanthan gum, pullulan, gellan gum, tragacanth gum, gum karaya, and combinations thereof. In some embodiments, the natural gum is a non-galactomannan polysaccharide selected from the group consisting of acacia gum, pullulan, gellan gum, and combinations thereof.

In some embodiments, the natural gum is a galactomannan polysaccharide. Examples of galactomannan polysaccharides which are natural gums include guar gum, fenugreek gum, tara gum, locust bean gum, and cassia gum. In some embodiments, the natural gum is a galactomannan polysaccharide selected from the group consisting of fenugreek gum, tara gum, locust bean gum, cassia gum, and combinations thereof.

In some embodiments, the natural gum is present in a range of from about 0.1% to about 80% by weight, for example, from about 0.1 to about 1%, about 1%, about 10%, about 20%, about 30%, about 40%, about 50%, about 60%, about 70%, or about 80% by weight, based on total weight of the oral composition. In some embodiments, the natural gum is present in a range of from about 0.1% to about 80% by weight, based on total weight of the oral composition. For example, in some embodiments, the natural gum is present in a range of from about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, or about 9%, to about 10%, about 15%, about 20%, about 25%, or about 30% by weight, based on total weight of the oral composition.

In some embodiments, the natural gum is a combination of guar gum and a second natural gum. In some embodiments, the second natural gum is selected from the group consisting of xanthan gum, pullulan, gellan gum, and combinations thereof.

In embodiments comprising a combination of natural gums, the ratio by weight of each natural gum in the combination may vary. For example, the ratio by weight of a galactomannan natural gum to a non-galactomannan natural gum may be from about 0.01 to about 10, such as about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 1, to about 2, about 3, about 4, about 5, about 6, about 7, about 8, about 9, or about 10. In some embodiments, the ratio by weight of a galactomannan natural gum to a non-galactomannan natural gum may be from about 0.1 to about 1.

In a specific embodiment, the natural gum is a combination of guar gum and a second natural gum selected from the group consisting of xanthan gum, pullulan, and gellan gum, wherein the ratio of guar gum to the second natural gum is from about 0.01 to about 10. In a specific embodiment, the natural gum is a combination of guar or locust bean gum with xanthan, wherein the ratio by weight of guar gum or locust bean gum to xanthan gum is from about 1 to about 10. In a specific embodiment, the natural gum is a combination of guar or locust bean gum with pullulan, wherein the ratio of guar or locust bean gum to pullulan is from about 1 to about 10. In a specific embodiment, the natural gum is a combination of guar, xanthan and pullulan wherein the ratio by weight of guar gum to xanthan gum to pullulan is from about 1:1:1 to about 10:1:1.

In some embodiments, the oral composition of the disclosure can be characterized as completely free or substantially free of xanthan gum. By "substantially free of xanthan gum" is meant that no xanthan gum has been intentionally added, beyond trace amounts that may be naturally present in e.g., another, non-xanthan natural gum. For example, certain embodiments can be characterized as having less than 0.001% by weight of xanthan gum, or less than 0.0001%, or even 0% by weight of xanthan gum.

In some embodiments, the polymeric component comprises a food grade polymer. By "food grade polymer" is meant that the polymer is approved for contact with food (e.g., a packaging material), or may be used in food (e.g. an edible polymer). By "edible polymer" is meant that the polymer may be consumed by a human, in whole or part, via the oral cavity with no harmful effect. The food grade polymers as described herein can be classified into three general categories: polysaccharides, proteins, and synthetic polymers.

In some embodiments, the food grade polymer is a polysaccharide which is not cellulosic and is not a natural gum. By "non-cellulosic polysaccharide" is meant a polysaccharide composed of several different types of unit monosaccharides, rather than the β(1→4) linked D-glucose polymer of which cellulose consists. Non-limiting examples of non-cellulosic polysaccharides which are not natural gums include hemicelluloses, starches, type II arabinogalactan (AG-II), chitin, and callose.

In some embodiments, the food grade polymer is a starch. "Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. Starches derived from various sources can be used. For example, major sources of starch include cereal grains (e.g., rice, wheat, and corn) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, yams, and sugar beet (e.g., FIBREX® brand filler available from International Fiber Corporation). Starch consists of two kinds of molecules, amylose (normally 20-30%) and amylopectin (normally 70-80%), which is primarily derived from cereal grains and tubers like corn, wheat, potato, tapioca, and rice. Amylose accounts for the film forming capacity of starch. Amylopectin possesses thickening and stabilizing properties. A specific starch can be selected for inclusion in the oral composition based on the ability of the starch material to impart a specific organoleptic property to the composition.

Certain starches are modified starches. A modified starch has undergone one or more structural modifications, often designed to alter its high heat properties. Some starches have been developed by genetic modifications, and are considered to be "genetically modified" starches. Other starches are obtained and subsequently modified by chemical, enzymatic, or physical means. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch.

Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropylated high amylose starch, hydroxypropyl distarch glycerol, starch sodium octenyl succinate, and maltodextrin.

Other suitable starches include alginate, carrageenan, dextrin, pectin, chitosan, hyaluronic acid, and combinations thereof. Alginates are polysaccharides derived from seaweeds which exhibit thickening, stabilizing, suspending, film forming, gel production, and emulsion stabilizing properties. Carrageenans are water-soluble polymers with a linear chain of partially sulfated galactans. These sulfated polysaccharides are extracted from the cell walls of various red seaweeds, and serve as viscosity increasing and gelling agents. In some embodiments, the food grade polymer is a starch selected from the group consisting of chitin, chitosan, carrageenan, alginate, pectin, and combinations thereof. In some embodiments, the food grade polymer is pectin.

In some embodiments, the polymeric component comprises a protein. Examples of suitable proteins include, but are not limited to, collagen, gelatin, casein, whey protein, rapeseed protein, zein, levan, elsinan, gluten, soy protein, rubisco, lentil protein, peanut protein, and mung bean protein. In some embodiments, the protein is casein, whey protein, soy protein isolate, collagen, or a combination thereof.

In some embodiments, the polymeric component comprises a synthetic polymer, meaning a polymer that is prepared by chemical means, is not found in nature, or both. Non-limiting examples of food grade synthetic polymers include polyethylene glycol, polypropylene glycol, polyvinyl alcohol, polyvinyl acetate, low density polyethylene, oriented polypropylene, polyethylene terephthalate, polyvinylidene chloride polyacrylic acid, polyacrylate, methyl methacrylate copolymer, carboxyvinyl polymer, anionic, cationic, and nonionic polyacrylamides, polyvinyl pyrrolidone, and poly-hydroxyacid polymer, such as polylactic acid, poly-3-hydroxybutyrate, poly-3-hydroxybutyrate cohydroxyvalerate, and the like. In some embodiments, the synthetic polymer is polyvinyl alcohol.

Filler

In some embodiments, the oral composition further comprises a filler. Similar to the role of the polymeric component, a filler may fulfill multiple functions, including enhancing certain organoleptic properties such as texture and mouthfeel, enhancing cohesiveness or compressibility of the composition, adding bulk to the composition, acting as a carrier for an active ingredient or flavorant, and the like.

When present, the amount of filler present on a weight basis can vary, but is typically up to about 90% of the total composition by weight. A typical range of filler within the oral composition can be from about 0.1% to about 90% by total weight of the composition, for example, from about 0.1 to about 1, or from about 1 to about 10, or from about 10 to about 90% by weight. In some embodiments, the filler is present in the oral composition in an amount by weight of from about 0.1 to about 1%, for example, about 0.1, about 0.2, about 0.3, about 0.4, about 0.5, about 0.6, about 0.7, about 0.8, about 0.9, or about 1% by weight, based on the total weight of the oral composition. In some embodiments, the filler is present in the oral composition in an amount by weight of from about 1 to about 10%, for example, about 1, about 2, about 3, about 4, about 5, about 6, about 7, about 8, about 9, or about 10% by weight, based on the total weight of the oral composition. In some embodiments, the filler is present in the oral composition in an amount by weight of from about 10 to about 90%, for example, about 10, about 15, about 20, about 25, or about 30, to about 35, about 40, about 45, about 50, about 55, about 60, about 65, about 70, about 75%, about 80%, about 85%, or about 90% by weight (e.g., about 15 to about 60% by weight, or about 25 to about 45% by weight) based on the total weight of the composition.

Non-limiting examples of potential fillers include cellulose, starch, calcium carbonate, calcium phosphate, lactose, dextrose, mannitol, xylitol, and sorbitol. Combinations of fillers can also be used. In some embodiments, the filler comprises cellulose, a starch, or a combination thereof. "Cellulose" as used herein refers to any non-tobacco plant material or derivative thereof, including cellulose derived from such sources, such as natural cellulose and modified cellulosic materials. One non-limiting example of a suitable cellulose material for use in the compositions described herein is microcrystalline cellulose ("MCC"). In one embodiment, the filler is MCC. In some embodiments, the MCC is present in an amount of from about 1% to about 60% by weight, based on the total weight of the composition. The MCC may be synthetic or semi-synthetic, or it may be obtained entirely from natural celluloses. The MCC may be selected from the group consisting of MCC available under the trademarks AVICEL® (grades PH-100, PH-102, PH-103, PH-105, PH-112, PH-113, PH-200, PH-300, PH-302); VIVACEL®) grades 101, 102, 12, 20); and EMOCEL® (grades 50M and 90M), and mixtures thereof.

In some embodiments, the filler comprises a cellulose derivative. By "cellulose derivative" is meant a cellulose material which has been chemically modified by reaction of one or more hydroxyl groups of the cellulose polymer structure with, for example, an esterifying or alkylating agent. Cellulose derivatives include, but are not limited to, any derivative of cellulose such as cellulose esters and cellulose ethers. By "cellulose ester" is meant a cellulose structure with the hydrogen of one or more hydroxyl groups in the cellulose polymer structure replaced with, for example, an acyl, nitro, or sulfate group. Cellulose esters may be organic esters (e.g., cellulose acetate, cellulose triacetate, cellulose propionate, cellulose acetate propionate (CAP), cellulose acetate butyrate (CAB)), or inorganic esters (e.g., nitrocellulose (cellulose nitrate), and cellulose sulfate). By "cellulose ether" is meant a cellulose structure with the hydrogen of one or more hydroxyl groups in the cellulose polymer structure replaced with an alkyl, hydroxyalkyl, or aryl group. Cellulose ethers include, for example, alkyl ethers (e.g., methyl cellulose, ethyl cellulose), hydroxyalkyl ethers (e.g., hydroxyethyl cellulose, hydroxypropyl cellulose (HPC), hydroxyethylmethyl cellulose, hydroxypropylmethyl cellulose (HMPC), ethylhydroxyethyl cellulose), and carboxyalkyl ethers (e.g., carboxymethylcellulose (CMC)).

Water

The water content of the oral composition, prior to use by a consumer, may vary according to the desired properties. Typically, water is present in the oral composition, prior to insertion into the mouth of the user, in an amount of at least about 10% by weight, and generally is from about 10 to about 60% by weight of water, for example, from about 10 to about 55%, about 15% to about 50%, about 20% to about 45%, or about 25% to about 40% water by weight, based on the total weight of the oral composition.

In some embodiments, the moisture content of the oral composition may be described in terms of water activity. As used herein, the term "water activity" or "Aw" refers to the partial vapor pressure of water in a composition divided by the partial vapor pressure of pure water at the same temperature. According to this definition, pure distilled water has an Aw of exactly one. The water activity of the oral composition may vary according to the form and desired properties, for example, from about 0.94 to about 0.65. Typically, the water activity will be less than about 0.85, for example, from about 0.85 to about 0.65, from about 0.85 to about 0.70, or from about 0.80 to about 0.75.

Active Ingredient

The oral composition as disclosed herein includes one or more active ingredients. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients (e.g., hemp, lavender, peppermint, eucalyptus, rooibos, fennel, cloves, chamomile, basil, rosemary, clove, citrus, ginger, *cannabis, Ginseng*, maca, and tisanes), stimulants (e.g., caffeine or guarana), amino acids (e.g., taurine, theanine, phenylalanine, tyrosine, and tryptophan), vitamins (B6, B12, and C), antioxidants, nicotine components, pharmaceutical ingredients (e.g., nutraceutical and medicinal ingredients), cannabinoids (e.g., tetrahydrocannabinol (THC) or cannabidiol (CBD)) and/or melatonin. Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species).

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include hemp, eucalyptus, rooibos, fennel, citrus, cloves, lavender, peppermint, chamomile, basil, rosemary, ginger, turmeric, green tea, white mulberry, *cannabis*, cocoa, ashwagandha, baobab, chlorophyll, *Cordyceps*, damiana, *Ginseng*, guarana, and maca. In some embodiments, the composition comprises green tea, turmeric, and white mulberry.

Ashwagandha (*Withania somnifera*) is a plant in the Solanaceae (nightshade) family. As an herb, Ashwagandha has found use in the Indian Ayurvedic system of medicine, where it is also known as "Indian Winter cherry" or "Indian *Ginseng*." In some embodiments, the active ingredient comprises ashwagandha.

Baobab is the common name of a family of deciduous trees of the genus *Adansonia*. The fruit pulp and seeds of the Baobab are consumed, generally after drying, as a food or nutritional supplement. In some embodiments, the active ingredient comprises baobab.

Chlorophyll is any of several related green pigments found in the mesosomes of cyanobacteria, as well as in the chloroplasts of algae and plants. Chlorophyll has been used as a food additive (colorant) and a nutritional supplement. Chlorophyll may be provided either from native plant materials (e.g., botanicals) or in an extract or dried powder form. In some embodiments, the active ingredient comprises chlorophyll.

*Cordyceps* is a diverse genus of ascomycete (sac) fungi which are abundant in humid temperate and tropical forests. Members of the *Cordyceps* family are used extensively in traditional Chinese medicine. In some embodiments, the active ingredient comprises *Cordyceps*.

Damiana is a small, woody shrub of the family Passifloraceae. It is native to southern Texas, Central America, Mexico, South America, and the Caribbean. Damiana produces small, aromatic flowers, followed by fruits that taste similar to figs. The extract from damiana has been found to suppress aromatase activity, including the isolated compounds pinocembrin and acacetin. In some embodiments, the active ingredient comprises damiana.

Guarana is a climbing plant in the family Sapindaceae, native to the Amazon basin. The seeds from its fruit, which are about the size of a coffee bean, have a high concentration of caffeine and, consequently, stimulant activity. In some embodiments, the active ingredient comprises guarana. In some embodiments, the active ingredient comprises guarana, honey, and ashwagandha.

*Ginseng* is the root of plants of the genus *Panax*, which are characterized by the presence of unique steroid saponin phytochemicals (ginsenosides) and gintonin. *Ginseng* finds use as a dietary supplement in energy drinks or herbal teas, and in traditional medicine. Cultivated species include Korean *Ginseng* (*P. Ginseng*), South China *Ginseng* (*P. notoginseng*), and American *Ginseng* (*P. quinquefolius*). American *Ginseng* and Korean *Ginseng* vary in the type and quantity of various ginsenosides present. In some embodiments, the active ingredient comprises *Ginseng*. In some embodiments, the *Ginseng* is American *Ginseng* or Korean *Ginseng*. In specific embodiments, the active ingredient comprises Korean *Ginseng*.

Maca is a plant that grows in central Peru in the high plateaus of the Andes Mountains. It is a relative of the radish, and has an odor similar to butterscotch. Maca has been used in traditional (e.g., Chinese) medicine. In some embodiments, the active ingredient comprises maca.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

In some embodiments, the active ingredient comprises caffeine. In some embodiments, the active ingredient comprises theacrine. In some embodiments, the active ingredient comprises a combination of caffeine and theacrine.

Amino Acids

In some embodiments, the active ingredient comprises an amino acid. As used herein, the term "amino acid" refers to an organic compound that contains amine ($-NH_2$) and carboxyl ($-COOH$) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-translational modification).

Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine.

When present, an amino acid or combination of amino acids (e.g., taurine, theanine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

In some embodiments, the amino acid is taurine, theanine, phenylalanine, tyrosine, tryptophan, or a combination thereof. In some embodiments, the amino acid is taurine. In some embodiments, the active ingredient comprises a combination of taurine and caffeine. In some embodiments, the active ingredient comprises a combination of taurine, caffeine, and guarana. In some embodiments, the active ingredient comprises a combination of taurine, maca, and *Cordyceps*. In some embodiments, the active ingredient comprises a combination of theanine and caffeine.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the composition.

In some embodiments, the vitamin is vitamin B6, vitamin B12, vitamin E, vitamin C, or a combination thereof. In some embodiments, the active ingredient comprises a combination of vitamin B6, caffeine, and theanine. In some embodiments, the active ingredient comprises vitamin B6, vitamin B12, and taurine. In some embodiments, the active ingredient comprises a combination of vitamin B6, vitamin B12, *Ginseng*, and theanine. In some embodiments, the active ingredient comprises a combination of vitamin C, baobab, and chlorophyll.

In certain embodiments, the active ingredient is selected from the group consisting of caffeine, taurine, GABA, theanine, vitamin C, lemon balm extract, *Ginseng*, citicoline, sunflower lecithin, and combinations thereof. For example, the active ingredient can include a combination of caffeine, theanine, and optionally *Ginseng*. In another embodiment, the active ingredient includes a combination of theanine, gamma-amino butyric acid (GABA), and lemon balm extract. In a further embodiment, the active ingredient includes theanine, theanine and tryptophan, or theanine and one or more B vitamins (e.g., vitamin B6 or B12). In a still further embodiment, the active ingredient includes a combination of caffeine, taurine, and vitamin C.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, *Ginseng*, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, *Withania somnifera*, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof. In some embodiments, the antioxidant is Vitamin E or a derivative thereof, a flavonoid, a polyphenol, a carotenoid, or a combination thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Nicotine Component

In certain embodiments, a nicotine component may be included in the oral composition. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, nicotine is in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.,* 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride. In some embodiments, the nicotine component or a portion thereof is a nicotine salt with at least a portion of the one or more organic acids as disclosed herein above.

In some embodiments, at least a portion of the nicotine can be in the form of a resin complex of nicotine, where nicotine is bound in an ion-exchange resin, such as nicotine polacrilex, which is nicotine bound to, for example, a polymethacrylic polymethacrilic acid resin, such as those available as Amberlite® IRP64, Purolite® C115HMR, or Doshion® P551. See, for example, U.S. Pat. No. 3,901,248 to Lichtneckert et al., which is incorporated herein by reference. In some embodiments, at least a portion of the nicotine may be present in the form of a nicotine-polyacrylic acid carbomer complex. An example of a suitable polyacrylic acid carbomer is the crosslinked polyacrylic acid carbomer available as Carbopol® 974P.

Typically, the nicotine component (calculated as the free base) when present, is in a concentration of at least about 0.001% by weight of the oral composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the oral composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the oral composition. These ranges can also apply to other active ingredients noted herein.

In some embodiments, the oral composition of the disclosure can be characterized as completely free or substantially free of nicotine components. By "substantially free of nicotine components" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in *cannabis*; and synthetic cannabinoids, manufactured artificially. Cannabinoids found in *cannabis* include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCV A). In certain embodiments, the cannabinoid is selected from tetrahydrocannabinol (THC), the primary psychoactive compound in *cannabis*, and cannabidiol (CBD) another major constituent of the plant, but which is devoid of psychoactivity. All of the above compounds can be used in the form of an isolate from plant material or synthetically derived.

Alternatively, the active ingredient can be a cannabimimetic, which is a class of compounds derived from plants other than *cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids.

When present, a cannabinoid (e.g., CBD) or cannabimimetic is typically in a concentration of at least about 0.1% by weight of the composition, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

Pharmaceutical Ingredients

The pharmaceutical ingredient can be any known agent adapted for therapeutic, prophylactic, or diagnostic use. These can include, for example, synthetic organic compounds, proteins and peptides, polysaccharides and other sugars, lipids, inorganic compounds, and nucleic acid sequences, having therapeutic, prophylactic, or diagnostic activity. Non-limiting examples of pharmaceutical ingredients include analgesics and antipyretics (e.g., acetylsalicylic acid, acetaminophen, 3-(4-isobutylphenyl)propanoic acid).

Flavorant

The oral composition as disclosed herein may comprise one or more flavorants. As used herein, a "flavorant" or "flavoring agent" is any flavorful or aromatic substance capable of altering the sensory characteristics associated with the smokeless tobacco composition. Examples of sensory characteristics that can be modified by the flavorant include taste, mouthfeel, moistness, coolness/heat, and/or fragrance/aroma. Flavorants may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/ cocoa, cream, mint, spearmint, menthol, peppermint, wintergreen, eucalyptus, lavender, cardamom, nutmeg, cinnamon, clove, cascarilla, sandalwood, honey, jasmine, ginger, anise, sage, licorice, lemon, orange, apple, peach, lime, cherry, strawberry, trigeminal sensates, terpenes, and any combinations thereof. See also, Leffingwell et al., Tobacco Flavoring for Smoking Products, R. J. Reynolds Tobacco Company (1972), which is incorporated herein by reference. Flavoring agents may comprise components such as terpenes, terpenoids, aldehydes, ketones, esters, and the like. In some embodiments, the flavoring agent is a trigeminal sensate. As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol. Flavorings also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, tropical, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form. In some embodiments, the flavorant comprises mint or fruit flavors. In certain embodiments, the flavorant is selected from the group consisting of mint, fruit flavors, limonene, star anise, eucalyptus, menthol, and combinations thereof.

The amount of flavorant utilized in the oral composition can vary, but is typically up to about 10 weight percent, and certain embodiments are characterized by a flavorant content of at least about 0.5 weight percent, such as about 0.5 to about 10 weight percent, about 1 to about 6 weight percent, or about 2 to about 5 weight percent, based on the total weight of the oral composition.

Salts

In some embodiments, the oral composition may further comprise a salt (e.g., alkali metal salts), typically employed in an amount sufficient to provide desired sensory attributes to the composition. Non-limiting examples of suitable salts include sodium chloride, potassium chloride, ammonium chloride, flour salt, and the like. When present, a representative amount of salt is about 0.5 percent by weight or more, about 1.0 percent by weight or more, or at about 1.5 percent by weight or more, but will typically make up about 10 percent or less of the total weight of the composition, or about 7.5 percent or less or about 5 percent or less (e.g., about 0.5 to about 5 percent by weight), based on the total weight of the oral composition.

Sweeteners

The oral composition typically further comprises one or more sweeteners. The sweeteners can be any sweetener or combination of sweeteners, in natural or artificial form, or as a combination of natural and artificial sweeteners. Examples of natural sweeteners include fructose, sucrose, glucose, maltose, isomaltulose, mannose, galactose, lactose, stevia, and the like. Examples of artificial sweeteners include sucralose, maltodextrin, saccharin, aspartame, acesulfame K, neotame and the like. In some embodiments, the sweetener comprises a sugar alcohol. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 20 percent or more of the of the oral composition by weight, for example, from about 0.1 to about 1%, from about 1 to about 5%, from about 5 to about 10%, or from about 10 to about 20% of the total composition on a weight basis.

Humectants

In certain embodiments, one or more humectants may be employed in the oral composition. Examples of humectants include, but are not limited to, glycerin, propylene glycol, and the like. Where included, the humectant is typically provided in an amount sufficient to provide desired moisture attributes to the oral composition. Further, in some instances, the humectant may impart desirable flow characteristics to the oral composition for depositing in a mold. When present, a humectant will typically make up about 5% or less of the weight of the oral composition (e.g., from about 0.5 to about 5%). When present, a representative amount of humectant is about 0.1% to about 1% by weight, or about 1% to about 5% by weight, based on the total weight of the oral composition.

Surfactants

In certain embodiments, the oral composition may be encapsulated, e.g., in the form of an emulsion such as a macro, micro, or nanoemulsion. To achieve emulsification of the components of the oral composition, one or more emulsifiers (i.e., surfactants) may be included in the oral composition. Non-limiting examples of emulsifiers include lecithin, sodium phosphates, polysorbates, sorbitan esters, mono and diacyl glycerides, sodium lauryl sulfate, and sodium stearyl lactate. Further, certain components referenced herein above (e.g., gum acacia, gum tragacanth, CMC, PEG, sorbitol, mannitol, maltitol, erythritol, xylitol, and humectants such as polyhydric alcohols, propanediol, and the like) may also be utilized as emulsifiers or other components (e.g., as stabilizers and the like) of an emulsified composition.

Buffering Agent

In certain embodiments, the oral composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Where present, the buffering agent is typically present in an amount less than about 5 percent based on the weight of the oral composition, for example, from about 0.5% to about 5%, such as, e.g., from about 0.75% to about 4%, from about 0.75% to about 3%, or from about 1% to about 2% by weight, based on the total weight of the oral composition. Non-limiting examples of suitable buffers include alkali metals acetates, glycinates, phosphates, glycerophosphates, citrates, carbonates, hydrogen carbonates, borates, or mixtures thereof.

Colorants

A colorant may be employed in amounts sufficient to provide the desired physical attributes to the oral composition. Examples of colorants include various dyes and pigments, such as caramel coloring and titanium dioxide. The amount of colorant utilized in the oral composition can vary, but when present is typically up to about 3% by weight, such as from about 0.1%, about 0.5%, or about 1%, to about 3% by weight, based on the total weight of the oral composition.

Tobacco Material

In some embodiments, the oral composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N.* x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *hersperis, N. pauciflora, N. petunioides, N. quadrivalvis, N. repanda, N. rotundifolia, N. solanifolia,* and *N. spegazzinii.* Various representative other types of plants from the *Nicotiana* species are set forth in Goodspeed, *The Genus Nicotiana,* (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology,* Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within an oral composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The oral composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the oral composition most preferably includes tobacco lamina, or a tobacco lamina and stem mixture (of which at least a portion is smoke-treated). Portions of the tobaccos within the oral composition may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the oral composition optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral products, it is typical for a harvested plant of the *Nicotiana* species to be subjected to a curing process. The tobacco materials incorporated within the oral compositions for inclusion within pouched products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; and U.S. Pat. No. 5,713,376 to Berger; and PCT WO 96/31255 to Giolvas, all of which are incorporated herein by reference. Other whitening methods using reagents such as ozone and potassium permanganate can also be used. See, for example, U.S. Pat. No. 3,943,940 to Minami, which is incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the final composition, with an example range of up to about 30% by weight, based on total weight of the oral composition (e.g., about 0.1 to about 15% by weight). In some embodiments, the products of the disclosure can be characterized as completely free or substantially free of tobacco material (other than purified nicotine as an active ingredient). For example, certain embodiments can be characterized as having less than 1% by weight, or less than 0.5% by weight, or less than 0.1%, or less than 0.1% by weight of tobacco material, or even 0% by weight of tobacco material. In other embodiments, the oral composition comprises tobacco. In some embodiments, the oral composition comprises up to about 5% of tobacco, for example, from about 0.1 to about 1%, or from about 1% to about 5% by weight of tobacco, based on the total weight of the oral composition. In some embodiments, the oral composition comprises a traditional tobacco or a white tobacco. In some embodiments, the tobacco is a white tobacco.

Other Additives

Other additives can be included in the disclosed oral composition. For example, the oral composition can be processed, blended, formulated, combined and/or mixed with other materials or ingredients. The additives can be artificial, or can be obtained or derived from herbal or biological sources. Examples of types of additives include gelling agents (e.g., fish gelatin), emulsifiers, oral care additives (e.g., thyme oil, eucalyptus oil, and zinc), preservatives (e.g., potassium sorbate and the like), antioxidants, disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., U.S. Pat. App. Pub. No. 2010/0291245 to Gao et al., and U.S. Pat. App. Pub. No. 2007/0062549 to Holton, Jr. et al., each of which is incorporated herein by reference. These and other exemplary types of additives may include those described in, for example, previously incorporated by reference herein. Typical inclusion ranges for such additional additives can vary depending on the nature and function of the additive and the intended effect on the final composition, with an example range of up to about 10% by weight, based on total weight of the oral composition (e.g., about 0.1 to about 5% by weight).

The aforementioned additives can be employed together (e.g., as additive formulations) or separately (e.g., individual additive components can be added at different stages involved in the preparation of the final oral composition). Furthermore, the aforementioned types of additives may be encapsulated as provided in the final product or oral composition. Exemplary encapsulated additives are described, for example, in WO 2010/132444 A2 to Atchley, which has been previously incorporated by reference herein.

In some embodiments, any one or more of a filler, a tobacco material, and the overall oral product described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, such as 300 μm.

In some embodiments, any particulate material referenced herein (e.g., filler, tobacco material, and the overall oral product) can be characterized as having at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 90% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 99% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 μm to about 1000 μm, such as from about 0.05 μm to about 750 μm, such as from about 0.1 μm to about 500 μm, such as from about 0.25 μm to about 500 μm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 μm to about 400 μm, such as from about 50 μm to about 350 μm, such as from about 100 μm to about 350 μm, such as from about 200 μm to about 300 μm.

Preparation of Oral Compositions

The manner by which the various components of the oral composition are combined may vary. As such, the overall oral composition comprising the various components, e.g., powdered components, may be relatively uniform in nature. The components noted above, which may be in liquid or dry solid form, can be admixed in a pretreatment step prior to mixing with any remaining components of the composition, or simply mixed together with all other liquid or dry ingredients. The various components may be contacted, combined, or mixed together using any mixing technique or equipment known in the art. Any mixing method that brings the components into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components are prepared such that the mixture thereof may be used in a starch molding process for forming the mixture. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

Configured for Oral Use

Provided herein is a product configured for oral use. The term "configured for oral use" as used herein means that the product is provided in a form such that during use, saliva in the mouth of the user causes one or more of the components of the oral composition (e.g., flavoring agents and/or active ingredients, such as nicotine) to pass into the mouth of the user. In certain embodiments, the product is adapted to deliver components to a user through mucous membranes in the user's mouth and, in some instances, said component is an active ingredient (including, but not limited to, for example, nicotine) that can be absorbed through the mucous membranes in the mouth when the product is used. In some embodiments, the component is a flavorant (e.g., a volatile flavor component).

Products configured for oral use as described herein may take various forms, including g gels, pastilles, gums, lozenges, powders, and pouches. Gels can be soft or hard. Certain products configured for oral use are in the form of pastilles. As used herein, the term "pastille" refers to a dissolvable oral product made by solidifying a liquid or gel composition so that the final product is a somewhat hardened solid gel. The rigidity of the gel is highly variable. Certain products of the disclosure are in the form of solids. Certain products can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouth-coating, roughness, slipperiness, smoothness, viscosity, wetness, and combinations thereof.

The products comprising the oral composition of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release compositions typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the oral composition. In some embodiments, the product can be meltable as discussed, for example, in US Patent App. Pub. No. 20120037175 to Cantrell et al. In other embodiments, the products do not dissolve during the product's residence in the user's mouth.

In one embodiment, the product comprising the oral composition of the present disclosure is in the form of an oral composition disposed within a moisture-permeable container (e.g., a water-permeable pouch). Such oral compositions in the water-permeable pouch format are typically used by placing one pouch containing the oral composition in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the oral composition therein (e.g., flavoring agents and/or nicotine) to pass through e.g., the water-permeable pouch and provide the user with flavor and satisfaction, and the user is not required to spit out any portion of the oral composition. After about 10 minutes to about 60 minutes, typically about 15 minutes to about 45 minutes, of use/enjoyment, substantial amounts of the oral composition have been absorbed through oral mucosa of the human subject, and the pouch may be removed from the mouth of the human subject for disposal.

Accordingly, in certain embodiments, the oral composition as disclosed herein and any other components noted above are combined within a moisture-permeable packet or pouch that acts as a container for use of the oral composition to provide a pouched product configured for oral use. Certain embodiments of the disclosure will be described with reference to FIG. 1 of the accompanying drawing, and these described embodiments involve snus-type products having an outer pouch and containing an oral composition as described herein. As explained in greater detail below, such embodiments are provided by way of example only, and the pouched products of the present disclosure can include oral composition in other forms. The composition/construction of such packets or pouches, such as the container pouch 102 in the embodiment illustrated in FIG. 1, may be varied. Referring to FIG. 1, there is shown a first embodiment of a pouched product 100. The pouched product 100 includes a moisture-permeable container in the form of a pouch 102, which contains a material 104 comprising an oral composition as described herein.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The oral composition may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the oral composition readily diffuse through the pouch and into the mouth of the user.

Non-limiting examples of suitable types of pouches are set forth in, for example, U.S. Pat. No. 5,167,244 to Kjerstad, which is incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and oral composition each may undergo complete dispersion within the mouth of the user during normal conditions of use, and hence the pouch and oral composition both may be ingested by the user. Other examples of pouch materials may be manufactured using water dispersible film forming materials (e.g., polymeric components such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the oral composition contents permeate through the pouch material prior to the time that the pouch undergoes loss of its physical integrity. If desired, flavoring ingredients, disintegration aids, and other desired components, may be incorporated within, or applied to, the pouch material.

The amount of oral composition contained within each product unit, for example, a pouch, may vary. In some embodiments, the dry weight of the oral composition within each pouch is at least about 50 mg, for example, from about 50 mg to about 2 grams, from about 100 mg to about 1.5 grams, or from about 200 to about 700 mg. In some smaller embodiments, the dry weight of the oral composition within each pouch may be from about 100 to about 300 mg. For a larger embodiment, the dry weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A pouched product comprising a moisture-permeable pouch and an oral composition enclosed therein, the oral composition comprising:

from about 0.1% to about 10% by weight of a nicotine component, calculated as the free base;

from about 0.1% to about 10% by weight of a natural gum selected from the group consisting of acacia gum, xanthan gum, guar gum, ghatti gum, pullulan, gellan gum, tragacanth gum, gum karaya, fenugreek gum, tara gum, locust bean gum, cassia gum, and combinations thereof;

from about 30% to about 55% by weight of microcrystalline cellulose; and at least one cellulose ether;

wherein the composition has a water content of from about 25% to about 55% by weight; and wherein the composition is free of tobacco material or comprises less than 0.1% by weight of tobacco material exclusive of the nicotine component, all weights above based on total weight of the oral composition.

2. The pouched product of claim 1, wherein the oral composition includes guar gum and at least one of xanthan gum, pullulan, or gellan gum, and wherein a ratio by weight of guar gum to the xanthan gum, or to the pullulan, or to the gellan gum, is from about 0.01 to about 10.

3. The pouched product of claim 1, comprising from about 0.5% to about 5% of a humectant by weight, based on the total weight of the oral composition.

4. The pouched product of claim 3, wherein the humectant is selected from the group consisting of glycerin, propylene glycol, and combinations thereof.

5. The pouched product of claim 1, comprising from about 0.5% to about 5% by weight of the natural gum, based on the total weight of the oral composition.

6. The pouched product of claim 1, further comprising from about 1% to about 10% by weight of one or more sweeteners, based on the total weight of the oral composition, the one or more sweeteners including at least one sugar alcohol.

7. The pouched product of claim 6, wherein the at least one sugar alcohol is selected from the group consisting of erythritol, arabitol, ribitol, isomalt, maltitol, dulcitol, iditol, mannitol, xylitol, lactitol, sorbitol, and combinations thereof.

8. The pouched product of claim 1, further comprising from about 0.5% to about 10% by weight of sodium chloride, based on the total weight of the oral composition.

9. The pouched product of claim 1, wherein the nicotine component is selected from the group consisting of free base nicotine, nicotine salts, and combinations thereof.

10. The pouched product of claim 1, wherein the cellulose ether is selected from the group consisting of methyl cellulose, ethyl cellulose, hydroxyethyl cellulose, hydroxypropyl cellulose, hydroxyethylmethyl cellulose, hydroxypropylmethylcellulose, ethylhydroxyethyl cellulose, carboxymethylcellulose, and combinations thereof.

11. The pouched product of claim 1, wherein the cellulose ether is carboxymethyl cellulose, hydroxypropylmethylcellulose, or a combination of carboxymethyl cellulose and hydroxypropylmethyl cellulose.

12. The pouched product of claim 1, wherein the nicotine component comprises a resin compleX of nicotine.

* * * * *